(12) United States Patent
Sugiyama

(10) Patent No.: US 6,540,963 B2
(45) Date of Patent: Apr. 1, 2003

(54) DETECTOR

(75) Inventor: Masahiro Sugiyama, Tokyo (JP)

(73) Assignee: Yamatake Corporation, Tokyo (JP)

( * ) Notice: Subject to any disclaimer, the term of this patent is extended or adjusted under 35 U.S.C. 154(b) by 0 days.

(21) Appl. No.: 09/881,228

(22) Filed: Jun. 11, 2001

(65) Prior Publication Data

US 2002/0006358 A1 Jan. 17, 2002

(30) Foreign Application Priority Data

Jun. 16, 2000 (JP) ........................................ 2000-181551

(51) Int. Cl.⁷ .............................................. G01N 27/00
(52) U.S. Cl. ........................... 422/98; 422/88; 422/110; 422/83
(58) Field of Search ............................. 422/98, 110, 88; 205/775; 73/23.31, 29.01, 335.02; 340/628; 338/35

(56) References Cited

U.S. PATENT DOCUMENTS 4,473,813 A * 9/1984 Kinjo et al. .................. 338/35
5,055,270 A * 10/1991 Consadori et al. ............ 422/98
5,369,995 A * 12/1994 Scheinbeim et al. ...... 73/335.02
5,689,059 A * 11/1997 Oh et al. .................... 73/23.31
5,728,289 A * 3/1998 Kirchnavy et al. .......... 205/775
5,729,207 A * 3/1998 Yamano ..................... 340/628

* cited by examiner

Primary Examiner—Jill Warden
Assistant Examiner—Brian Sines
(74) Attorney, Agent, or Firm—Frishauf, Holtz, Goodman & Chick, P.C.

(57) ABSTRACT

A humidity sensor 10 with high assembling properties and environmental resistance comprises a detecting element 14 having electrodes 14a and 14b formed on a base, conducting wires 12 and 13 connected individually to the electrodes by means of resin conductors formed of an organic high-molecular resin having an electrically conductive material dispersed therein, and a holding member 11 of an organic high-molecular resin for holding the detecting element and the conducting wires. The holding member has a connecting aperture 11c through which junctions between the electrodes and the conducting wires are exposed.

19 Claims, 6 Drawing Sheets

DETECTOR

BACKGROUND OF THE INVENTION

1. Field of the Invention

The present invention relates to a detector provided with a detecting element in a holding member and in which lead wires connected electrically to the detecting element are led out of the holding member.

2. Prior Art

In general, a humidity detector of an air conditioning duct insertion type for measuring the humidity in a room is provided with a humidity sensor. In this humidity sensor, a sensor element is set in a casing in the form of a metallic can, for example, and the detection output of the sensor element is taken out of the casing by means of lead wires.

The can-type humidity sensor is provided with a holder that is composed of a metallic base and metallic header. The base is fitted with the lead wires by means of a hermetic seal for insulation. In assembling the sensor, a sensor chip is mounted on the base, electrodes of the sensor chips and the end portions of the lead wires are connected electrically to one another by means of resin conductors, and thereafter, the header is put on and welded to the base to be packaged.

In some cases, in assembling the can-type humidity sensor, an operator may accidentally touch a moisture-responsive surface of the sensor chip by his/her fingers as he/she mounts the sensor chip on the base. In consequence, sebum on the fingers may possibly adhere to the moisture-responsive surface, thereby lowering the performance of the humidity sensor.

Since the header and the base are welded together after the electrodes and the lead wires are connected to one another by means of the-resin conductors, moreover, heat of the welding may be transmitted to resin conductor bonding portions. Accordingly, there is a possibility of the resin conductors being melted to hinder conduction between the electrodes and the lead wires.

Possibly, moreover, a holding member of the sensor chip may be formed of a plastic material. In this case, however, it is necessary to solder the sensor chip and conducting wires in advance and attach the resulting subassembly to the holding member, in order to prevent the holding member from being deformed by heat that is produced as the sensor chip and the conducting wires are soldered. However, this subassembly, composed of the sensor chip and the conducting wires connected by soldering, is low in mechanical strength. In consequence, the conducting wires may bend or coming off the sensor chip in some subsequent process of assembly. Thus, the operator must be cautious in handing the subassembly, so that the efficiency of assembly operation is very poor.

In an alternative can-type humidity sensor, electrodes and lead wires are normally in direct contact with one another, and a conductive resin is used to surround their junctions to secure electrical connection between them. In this case, however, prolonged use of the humidity sensor sometimes causes the electrodes and the lead wires to move relatively to one another, thereby changing the electrical resistance between their contact surfaces inevitably. In some cases, moreover, the electrical resistance between the contact surfaces may be changed by oxidation of the respective surfaces of the electrodes and the lead wires. Owing to these factors, the output of the conventional humidity sensor tends to change with time.

Conventionally, furthermore, there has been a problem that is attributable to the poor working environment of the humidity sensor. More specifically, air with humidity higher than a certain degree continually flows in air conditioning ducts for a heated indoor swimming pool or greenhouse, the environmental conditions for these ducts are poor. If the aforesaid can-type humidity sensor is subjected to these environmental conditions for a long period of time, the metallic casing or metallic parts surrounding the hermetic seal may be corroded, possibly causing a short circuit.

Although these problems have been described in connection with the can-type humidity sensor by way of example, it is to be understood that a can-type temperature sensor are subject to the same problems.

OBJECT AND SUMMARY OF THE INVENTION

The object of the present invention is to provide a detector improved in assembling properties and environmental resistance.

In order to achieve the above object, a detector according to the present invention comprises a detecting element having electrodes formed on a base, conducting wires connected individually to the electrodes by means of resin conductors formed of an organic high-molecular resin having an electrically conductive material dispersed therein, and a holding member of an organic high-molecular resin for holding the detecting element and the conducting wires, the holding member having a connecting aperture through which junctions between the electrodes and the conducting wires are exposed.

In assembly operation, the electrodes and the conducting wires are connected to one another through the connecting aperture after the detecting element is incorporated into the plastic holding member. Accordingly, the junctions between the electrodes and the conducting wires can be prevented from being broken during the assembly operation.

Since the electrodes and the conducting wires are connected to one another in a manner such that the resin conductors are applied through the connecting aperture after the detecting element is set in the holding member, moreover, the assembly operation involves no high-temperature operation such as soldering. Thus, the holding member, formed of the organic high-molecular resin, cannot be adversely affected by high temperature.

Another detector according to the invention comprises a detecting element having electrodes formed on a base, conducting wires connected individually to the electrodes by means of resin conductors formed of an organic high-molecular resin having an electrically conductive material dispersed therein, and a holding member of an organic high-molecular resin for holding the detecting element and the conducting wires, the electrodes and the conducting wires being kept at a given space from one another.

If the electrodes of the detecting element and the lead wires are brought directly into contact with one another for electrical conduction, the value of contact resistance varies substantially. In the detector of the invention, however, the electrodes of the detecting element and the lead wires are kept at the given space and are connected electrically to one another by means of the resin conductors. In consequence, the variation of the contact resistance value is lessened, so that the detection characteristics of the detector can be kept constant.

In the detector of the invention, moreover, the resin conductors having some elasticity are interposed between the electrodes and the resin conductors. In consequence, the value of contact resistance between the electrodes of the detecting element and the lead wires can be prevented from being changed with time by vibration during prolonged use of the detector.

Preferably, in the detector of the invention, the holding member is formed having a loading aperture through which the detecting element is inserted slidingly.

An operator can assemble the detector without unduly touching the detecting element with his/her fingers, so that the yield of assembly of the detector is improved.

Preferably, in the detector of the invention, the holding member is formed having an elastically deformable retaining portion for holding the detecting element.

Owing to the latching action of the retaining portion, the detecting element can be held securely in the holding member.

Preferably, in the detector of the invention, the conducting wires are molded integrally with the holding member.

In assembling the detector, the lead wires need not be inserted into the holding member, so that the assembling properties are improved. Further, the electrodes of the detecting element and the lead wires can be fixedly spaced when the detecting element is held in the holding member. Thus, the value of resistance between the electrodes and the lead wires conductors can be kept constant individually, so that the properties of the detecting element can be stabilized.

Preferably, in the detector of the invention, the holding member is formed having a hole through which the lead wires are inserted.

Since the lead wires need not be molded integrally with the holding member in advance, the molding cost can be lowered.

Preferably, in the detector of the invention, the holding member is formed having a ventilation aperture through which the detecting element is exposed to the outside air, and the holding member is formed having a protecting portion of the detecting element between the ventilation aperture and the connecting aperture.

This arrangement facilitates the maintenance of the quality of the detector, e.g., a humidity sensor, in which communication with the outside air is essential to the improvement of its detection characteristics and the detection characteristics lower considerably if the detecting element is touched by fingers.

Preferably, in the detector of the invention, the holding member is provided with a closing member for closing the connecting aperture.

In the case of a detector such as a temperature sensor that never strictly requires communication with the outside air, the assembly of the detector can be facilitated by closing the connecting aperture with the closing member, and the detecting element can be protected securely after the detector is assembled.

Preferably, in the detector of the invention, the ventilation aperture and the connecting aperture are covered by means of a porous filter.

With this arrangement, communication with the outside air can be secured to improve the detection characteristics, and the detecting element itself can be protected against waterdrops, dust, etc.

Preferably, in the detector of the invention, air passages capable of facilitating ventilation between the front and rear faces of the detecting element are defined between the detecting element and the holding member.

The detection response can be enhanced by improving the ventilation around the detecting element.

Preferably, in the detector of the invention, the holding member is formed having a push-up portion for keeping the detecting element at a fixed height level above the surface of the base on which the detector is mounted.

Since the detecting element can always be mounted at the fixed height level above the base surface, it never fails to be located in an optimum measuring position.

Preferably, in the detector of the invention, the detecting element is formed having a moisture-responsive surface for humidity detection on one side face thereof, and each of the conducting wires has one end conducting to the electrode on one side face of the detecting element and the other end led out of the holding member so as to extend substantially flush with the other side face of the detecting element.

Out of the electrodes of the detecting element, the electrode on the front or upper side is connected to the ground on the circuit, so that static electricity can be discharged from the upper electrode through the conducting wire on the ground side if it is externally discharged toward the detector. In consequence, high voltage cannot be applied to the moisture-responsive surface, so that the detecting element itself cannot be adversely affected.

Preferably, in the detector of the invention, a projection capable of preventing the holding member from falling down when the holding member is mounted on the base with the wire outlet surface in contact with the base is formed flush with the wire outlet surface.

In the case where the detector is mounted upright on the base surface, the projection can prevent the detector and the lead wires from being leveled on the base surface or broken by external force or vibration. Further, the projection serves to position the detector as the detector is mounted on the base surface.

Preferably, in the detector of the invention, the conducting wires include two lead wires attached substantially parallel to the holding member, the pitch between extending portions of the lead wires extending from the holding member being different from the pitch between resin conductor bonding portions of the lead wires.

The pitch between the resin conductor bonding portions of the lead wires can be adjusted to facilitate the attachment of the resin conductors without being restricted by the pitch between the extending portions of the lead wires from the holding member.

DETAILED DESCRIPTION OF THE INVENTION

A humidity sensor (detector) according to one embodiment of the present invention will now be described with respect to the accompanying drawings.

Figure 1:
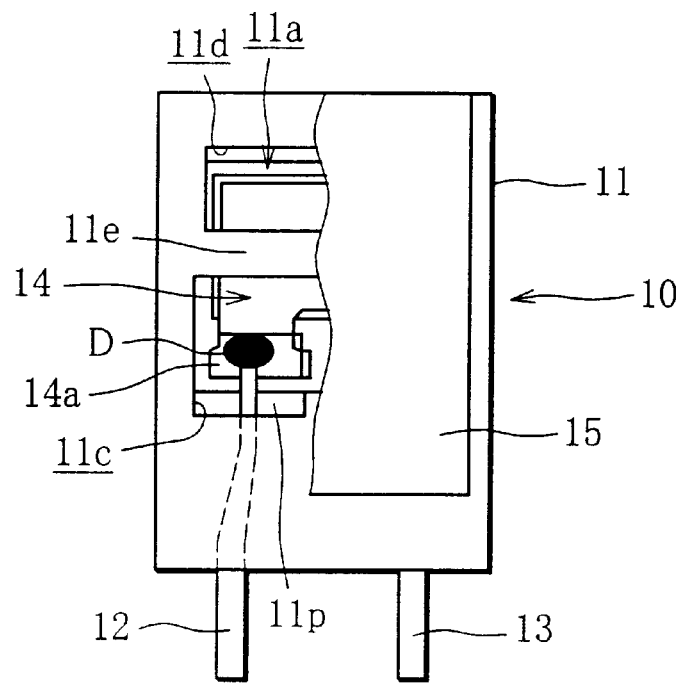
FIG. 1 is a front view showing a humidity sensor according to one embodiment of the present invention with a filter partially removed.

As shown in FIG. 1, a humidity sensor 10 according to one embodiment of the invention comprises a holder (holding member) 11, two lead wires (conducting wires) 12 and 13 molded integrally with the holder 11, a sensor element (detecting element) 14 connected to the lead wires 12 and 13 by means of resin conductors D (such as Dotite from Fujikara Kasei Co., Ltd.), an air filter (only partially shown in FIG. 1) 15 that covers a part of the holder 11, and the like.

Figure 3:
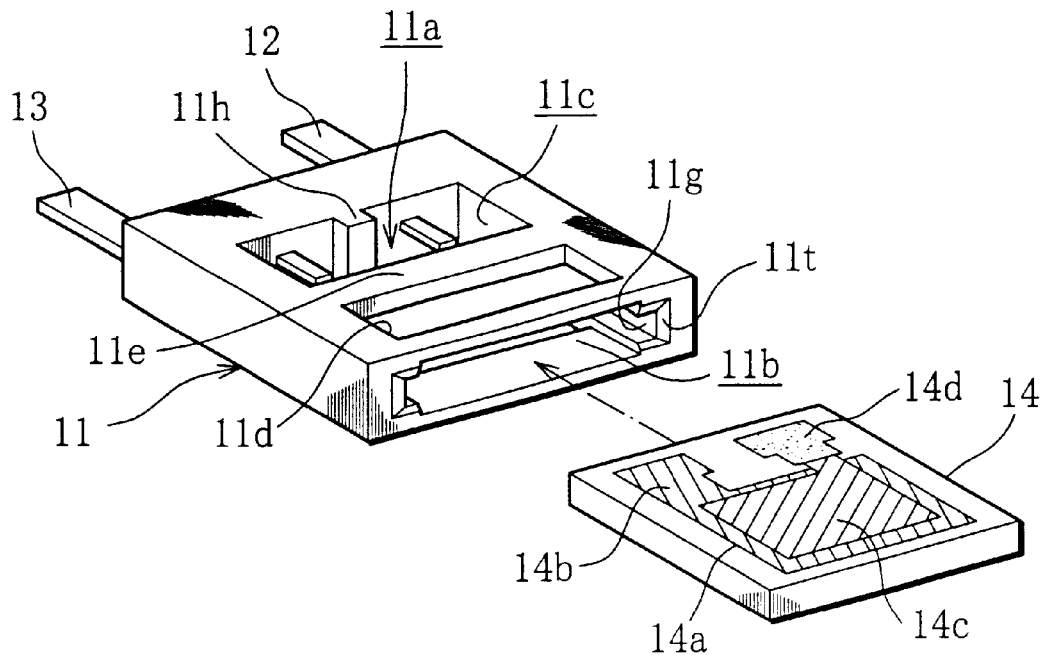
FIG. 3 is a schematic perspective view showing the way the humidity sensor of FIG. 1 is inserted into the holder.

The holder 11, which is formed of a molded product of a high-molecular resin such as PBT (polybutylene terephthalate), has an external shape that resembles a rectangular parallelepiped, as shown in FIGS. 1 and 3.

As shown in FIG. 3, moreover, the holder 11 has a sensor element storage portion 11a inside. A loading aperture 11b through which the sensor element 14 is inserted into the holder 11 is formed in one side face of the holder 11. The loading aperture 11b is formed having a taper portion 11t that facilitates the insertion of the sensor element 14. Guides 11g (only one of which is shown in FIG. 3) for sliding insertion in the sensor element storage portion 11a are formed individually on the opposite sidewalls storage portion 11a. Further, a connecting aperture 11c for connection between electrodes 14a and 14b of the sensor element 14 and the lead wires 12 and 13 are formed in the front face of the holder 11 (on the side for connection between the lead wire 12 (13) and the electrode 14a (14b) in FIG. 1). Furthermore, a ventilation aperture 11d for facilitating ventilation for the sensor element 14 is formed at a given distance from the connecting aperture 11c in the front face of the holder 11. A bridge portion that is formed between the connecting aperture 11c and the ventilation aperture 11d of the holder 11 constitutes a sensor element protecting portion 11e.

Figure 4:
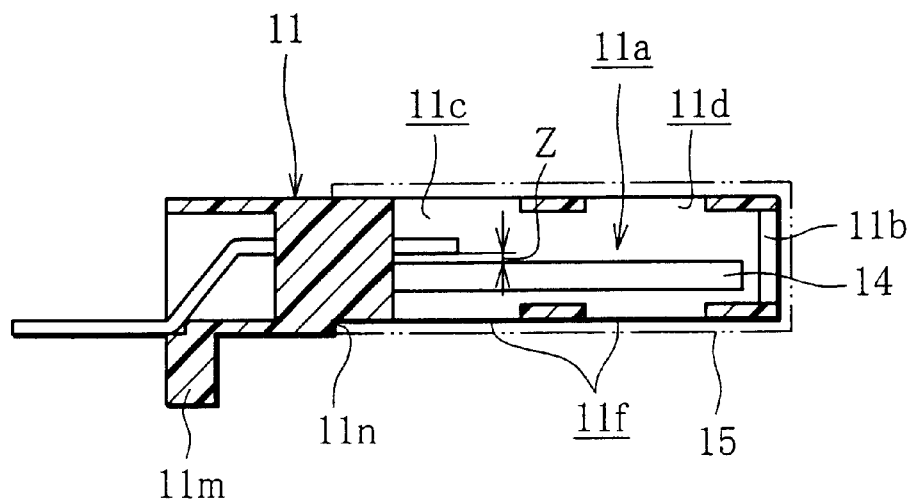
FIG. 4 is a schematic sectional view showing a state immediately before resin conductors are applied after a sensor element is inserted into the holder of FIG. 1.

As shown in FIG. 4, on the other hand, an aperture 11f is formed also in the rear face of the holder 11, corresponding in position to the connecting aperture 11c and the ventilation aperture 11d in the front face of the holder.

Figure 2:
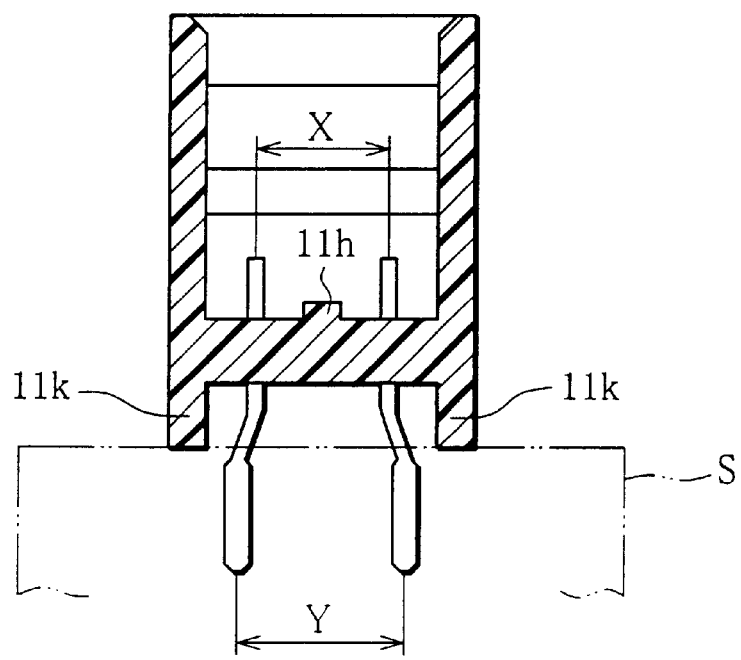
FIG. 2 is a front view, partially in section, showing a holder for the humidity sensor of FIG. 1.

As shown in FIGS. 2 and 3, a projection 11h is formed on the central portion of the bottom of the sensor element storage portion 11a. The projection 11h is adapted to define vent lines 11p (see FIG. 1) for the ventilation of the front and rear faces of the sensor element 14 on its opposite sides as the leading end portion of the element 14 abuts against it when the element 14 is set in the holder 11.

As shown in FIG. 2, moreover, the lead wire outlet side of the holder 11 is formed having a push-up portion 11k that surround the lead wires 12 and 13, whereby the sensor element 14 is separated at a given distance from the surface of a base S (indicated by two-dot chain line in FIG. 2). The push-up portion 11k allows the sensor element 14 to be exposed to an atmosphere that is distant enough from the base S, thereby improving the detection characteristics of the sensor element 14.

Figure 5A:
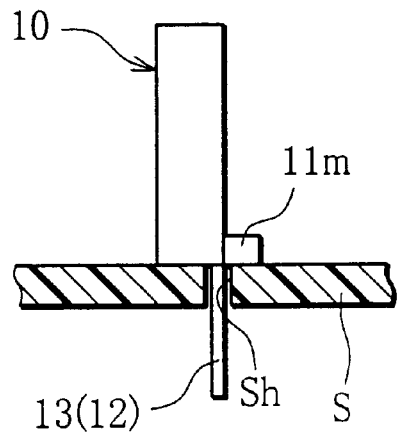
FIG. 5A is a side view showing the humidity sensor of FIG. 1 set up on a base.
Figure 5B:
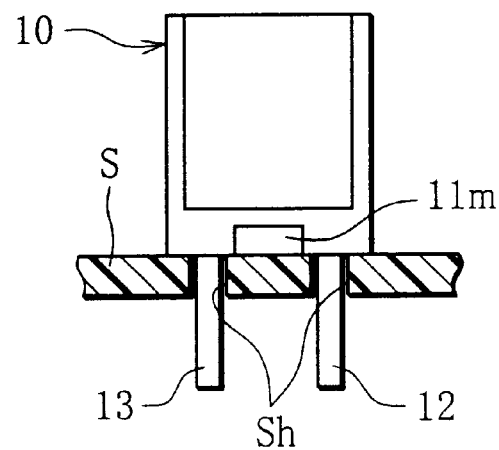
FIG. 5B is a front view showing the humidity sensor of FIG. 1 set up on the base.

As shown in FIGS. 5A and 5B, on the other hand, a safety projection 11m against the humidity sensor's overturning is formed on the rear face of the holder 11 so as to extend flush with the lead wire outlet surface of the holder 11. As mentioned later, the projection 11m serves also as a positioning portion when the humidity sensor 10 is mounted with its rear face in contact with the base S.

The holder 11 may be formed of any organic high-molecular material. Preferably, however, it should be formed of a liquid crystal polymer (LCP) with high thermal resistance, since the resin conductors D that connect the lead wires 12 and 13 and the electrodes 14a and 14b must be thermoset.

Each of the lead wires 12 and 13 is formed of a conventional conducting wire that is plated with phosphor bronze. As shown in FIGS. 1 and 2, each lead wire has a bent portion in the center, and its holder-storage-side end portion is narrower than its outlet-side end portion extending from the holder 11. Thus, the lead wires 12 and 13 are molded integrally with the holder 11 in a manner such that a pitch X (see FIG. 2) between the respective end portions of the wires 12 and 13 on the resin conductor bonding side is shorter than a pitch Y (see FIG. 2) between the respective end portions of the wires 12 and 13 that extend from the holder 11. Since the respective holder-storage-side end portions of the lead wires 12 and 13 are thus biased toward the central axis of the holder 11, long enough distances are secured between the edge portion of the connecting aperture 11c of the holder 11 and the lead wires. As shown in FIG. 4, moreover, each lead wire is molded integrally with the holder 11 in a manner such that its holder-storage-side end portion is kept at a given space Z (e.g., 0.2 mm) from the electrode on one side face (upper surface in FIG. 4) of the sensor element 14 and that the other end is bent so as to extend substantially flush with the other side face of the element 14.

In the case of the present embodiment, the sensor element 14 in the holder 11 is a detecting element for measuring the humidity of the atmosphere around the humidity sensor. The element 14 is in the form of a rectangular plate. The element 14 is formed with a lower electrode 14a of platinum or the like on an insulating substrate of aluminum or glass. Further, the sensor element 14 is provided with a moisture-responsive film (not shown) that covers the whole surface of the lower electrode 14a except the connecting terminal portion 14b of the electrode 14a. Furthermore, the sensor element 14 is formed with a moisture-permeable upper electrode 14c of gold, chromium or the like on the moisture-responsive film. A thin platinum film for reinforcement is formed on a connecting terminal portion 14d of the upper electrode (see FIG. 3). The moisture-responsive film is formed of PES (polyether sulfone) or a high-molecular moisture-responsive material that consists mainly of PES.

The moisture-responsive film absorbs water in air through the upper electrode 14c, whereupon the dielectric constant of the moisture-responsive film changes. Thus, the humidity can be measured by detecting the change of capacitance between the upper and lower electrodes 14c and 14a. The humidity can be measured by detecting the change of electrical resistance as well as by detecting the change of capacitance. However, the present invention is applicable without regard to the principle of measurement.

The lead wires 12 and 13 are molded integrally with the holder 11, and the sensor element 14 can be inserted into the holder 11 along a sensor element storage guide of the holder 11. As mentioned before, therefore, each lead wire 12 (or 13) and each electrode 14a (or 14b) are kept at the fixed distance Z from each other and never directly touch each other.

Further, the lower and upper electrodes 14a and 14b are connected to the lead wires 12 and 13, respectively, by means of the resin conductors D.

The humidity of the atmosphere around the humidity sensor is measured by detecting the change of the electric capacity value of the moisture-responsive film.

The conductive resin as the material for connecting the lead wires 12 and 13 and the electrodes 14a and 14b may be replaced with a conductive adhesive in which a conductive filler, such as metallic powder or carbon, is dispersed. In consideration of poor working environment, however, an epoxy-based conductive adhesive should preferably be used as the connecting material for the lead wires 12 and 13 and the electrodes 14a and 14b of the humidity sensor 10.

The air filter 15 is stuck to the front and rear faces of the holder 11 so as entirely to cover the connecting aperture 11c and the ventilation aperture 11d in the front face of the holder 11 and the aperture 11f in the rear face. The filter 15 is formed of a porous film sheet of Teflon (polytetrafluoroethylene). This porous film sheet allows air outside the humidity sensor to permeate the sensor element storage portion 11a, while it hardly allows dust or water-drops to be transmitted to the sensor element storage portion 11a from outside the humidity sensor. A step portion 11n is previously formed on the underside of the holder so that the whole rear face of the holder except the projection 11m is substantially flush when the air filter 15 is stuck to the holder 11 (see two-dot chain line of FIG. 4). Thus, the efficiency of operation for mounting the humidity sensor 10 with its rear face in contact with the base S is improved.

The following is a description of steps of procedure for assembling the humidity sensor 10 constructed in this manner.

First, the holder 11, having the lead wires 12 and 13 molded integrally therewith, is placed on a workbench in a manner such that the connecting aperture 11c faces upward, as shown in FIG. 3.

Then, an operator holds an edge portion of the sensor element 14 and inserts the element 14 into the holder 11 through the loading aperture 11b of the holder. In this case, the taper portion 11t of the loading aperture 11b and the element sliding guides 11g of the element storage portion 11a of the holder 11 facilitate the insertion.

After the sensor element 14 is inserted so that it abuts against the projection 11h (see FIG. 3) of the element storage portion 11a of the holder 11, as shown in FIG. 4, each resin conductor D is applied to the gap between the lead wire 12 (13) and the electrode 14a (14b), as shown in FIG. 1.

Since the respective element-storage-side ends of the lead wires 12 and 13 are biased toward the central axis of the holder 11, they are distant enough from the edge portion of the connecting aperture 11c of the holder 11, so that the resin conductors D can be applied with ease.

Subsequently, the holder 11 having undergone the aforesaid operation is heated to a temperature of 150° C. in a heating time of 30 minutes to 1 hour so that the resin conductors D are set, whereupon the connection between the lead wires 12 and 13 and the electrodes 14a and 14b of the sensor element 14 is completed.

As mentioned before, the lead wires 12 and 13 are molded integrally with the holder 11, and the sensor element 14 is slidably held by means of the guides 11g of the holder 11. Therefore, the respective end portions of the lead wires 12 and 13 and the electrodes of the sensor element 14 are always kept at fixed spaces from one another. Thus, the lead wires 12 and 13 and the electrodes 14a and 14b of the sensor element 14 are assembled so that they never fail to be connected electrically to one another through the resin conductors D without directly touching one another.

Further, the air filter 15 is stuck to the holder 11 so as to cover the connecting aperture 11c and the ventilation aperture 11d in the front face of the holder and the aperture 11f in the rear face of the holder, whereupon assembling the humidity sensor 10 is finished.

According to the humidity sensor 10 of the foregoing embodiment of the present invention, as is evident from the above description, the holder 11 is formed of plastics, and the sensor element 14 is stored and held in the holder. Accordingly, this humidity sensor does not require any packaging by welding that is required by a conventional can-type humidity sensor, and can never be thermally influenced by the packaging process.

Since the sensor element 14 is slid through the loading aperture 11b of the holder 11 as it is inserted into the holder, moreover, there is hardly any possibility of the operator accidentally touching a humidity sensing portion of the element 14 as he/she sets the element 14 in position.

Further, the lead wires 12 and 13 are molded integrally with the holder 11 in advance, and the holder 11 is formed having the guides 11g for sensor element insertion. Therefore, the lead wires 12 and 13 and the electrodes 14a and 14b can be located at given spaces by only inserting the sensor element 14 into the holder 11. Furthermore, the lead wires 12 and 13 and the electrodes 14a and 14b are connected to one another by only applying the resin conductors D to the gaps between them. Accordingly, a conventional process for soldering the lead wires 12 and 13 and the sensor element 14 before attaching the humidity sensor can be omitted. Thus, breakage of the connecting portion during the subsequent attachment process, which has conventionally been a problem, can be prevented.

The holder 11 is provided with the connecting aperture 11c through which the resin conductors D are applied to the gaps between the lead wires 12 and 13 and the electrodes 14a and 14b of the sensor element. Besides, the respective end portions of the two lead wires on the side of the sensor element storage portion of the holder 11 are molded integrally with the holder 11 so that the space between them is narrow. Thus, the resin conductors D can be applied with ease. In applying the resin conductors D, moreover, the operator can avoid directly touching the detecting portion of the sensor element 14. Further, the resin conductor applying operation can be automated.

The air filter 15 covers the connecting aperture 11c and the ventilation aperture 11d in the front face of the holder 11 and the aperture 11f in the rear face of the holder. Thus, dust and water can be prevented from getting into the sensor element storage portion 11a of the holder 11, so that a moisture-responsive portion and electrode portion of the sensor element 14 can be protected.

In the sensor element storage portion 11a of the holder 11, moreover, the sensor element 14 is in contact with the projection 11h in the center of the bottom portion of the storage portion. Thus, passages 11p for ventilating the front and rear faces of the sensor element 14 are formed individually on the opposite sides of the projection 11h (see FIG. 1), so that the change of humidity of the atmosphere around the humidity sensor can be detected with good response.

Further, the bridge portion is formed between the connecting aperture 11c and the ventilation aperture 11d in the front face of the holder 11, and constitutes the sensor element protecting portion 11e. In mounting the humidity sensor 10 on the base S, therefore, the operator can hold it with excessive force without breaking the sensor element 14.

As is evident from the above description, the humidity sensor 10 can be easily assembled without using any special tool. Further, it can be automatically assembled by means of an automatic machine.

The following is a description of a process for mounting the assembled humidity sensor 10 on the base S.

In mounting the humidity sensor 10, it is set up on the base S in a manner such that the lead wires 12 and 13 can be inserted into lead wire holes Sh, individually, as shown in FIGS. 5A and 5B. Preferably, projecting portions of the lead wires should be soldered by solder flowing or the like after the humidity sensor 10 is tacked on the base S with an adhesive.

In a conventional humidity sensor, lead wires are adjusted to an appropriate length of projection by using a special spacer. In the case of the humidity sensor 10 according to the present embodiment, however, the holder 11 is formed with the push-up portion 11k (see FIG. 2), so that the length of projection of the lead wires 12 and 13 from the holder 11 has an appropriate value. In consequence, attachment of the spacer is unnecessary, so that the man-hour for assembly can be lessened.

If the humidity sensor 10 is mounted upright on the base S, the lead wires 12 and 13 never project unduly, so that it is unnecessary to cut redundant lead wires.

If the humidity sensor 10 is mounted with its rear face in contact with the base S, moreover, the projecting portions of the lead wires 12 and 13 never project from regions for solder pads.

If the humidity sensor 10 is mounted upright on the base S, furthermore, the push-up portion 11k serves to separate the sensor element 14 fully from the base surface. In consequence, the element 14 can be exposed to the ambient atmosphere, so that the detection characteristics are improved. Besides, the push-up portion 11k serves to prevent breakage of the lead wires 12 and 13 that is attributable to local bending.

In the case where the humidity sensor 10 is mounted on the base S in this manner, the projection 11m (see FIG. 5) that extends flush with the lead wire outlet surface of the holder 11 can prevent the sensor 10 from falling down if any external force acts on the sensor 10. Thus, the lead wires 12 and 13 that are led out of the humidity sensor 10 can be protected securely.

Figure 6:
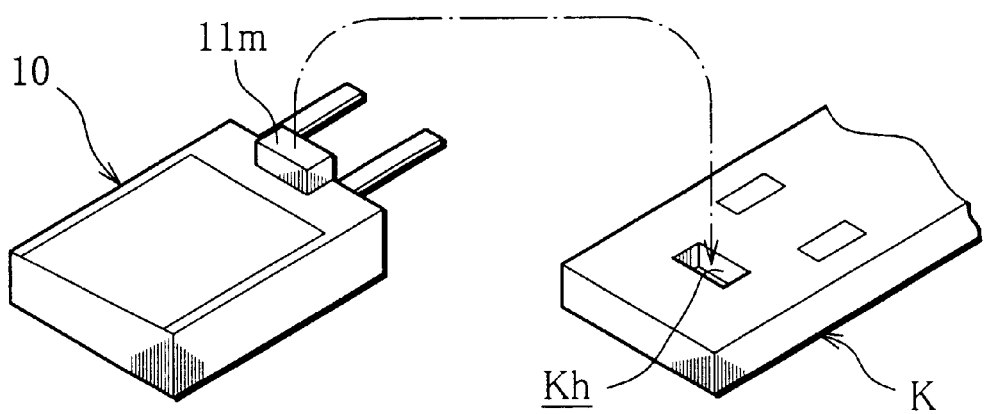
FIG. 6 is a schematic perspective view illustrating a mounting method such that the rear face of the humidity sensor of FIG. 1 is brought into contact with a base.

In the case where the humidity sensor 10 is mounted with its rear face in contact with a base K, as shown in FIG. 6, on the other hand, the projection 11m serves as a positioning projection that mates with a humidity sensor mounting hole Kh of the base K. In consequence, the humidity sensor 10 can be securely mounted in a given position on the base K.

After the humidity sensor 10 is mounted on the base S (or base K) in this manner, the base is attached to a protective pipe (not shown) of an insertion-type humidity detector. Thereafter, the humidity detector is fitted with a protective filter, protective cap (not shown), etc., whereupon its assembly is completed.

The insertion-type humidity detector constructed in this manner is attached to a duct of air conditioning equipment and used to measure the humidity of air in the duct.

In the humidity sensor 10 according to the embodiment described above, the air filter 15 covers the connecting aperture 11c and the ventilation aperture 11d of the holder 11. However, the humidity sensor need not always be provided with the air filter 15 if it is used in an environment that requires neither of dustproof and waterproof measures.

The air filter 15 is not essential either if the sensor element 14 according to the foregoing embodiment is replaced with a detecting element for temperature or the like that requires neither of dustproof and waterproof measures.

Figure 7:
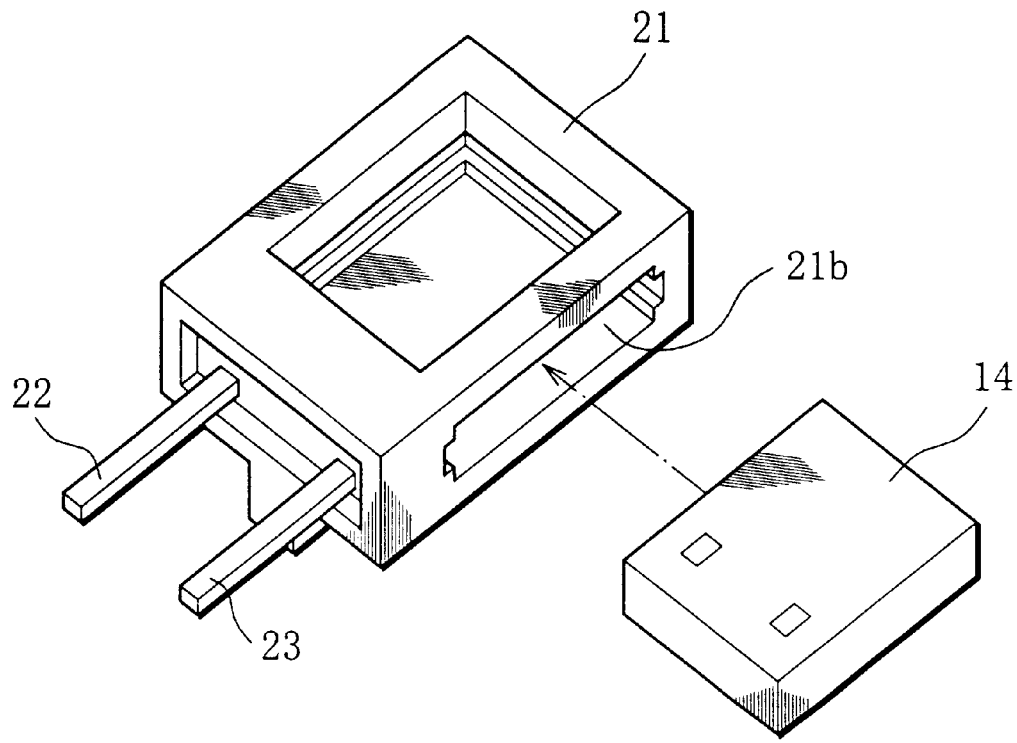
FIG. 7 is a schematic perspective view showing a modification of the humidity sensor according to aforesaid embodiment of the invention.

Instead of using the humidity sensor 10 according to the foregoing embodiment, moreover, a holder 21 may be provided with a sensor element loading aperture 21b on its side face that adjoins its lead wire outlet surface, as shown in FIG. 7. Thus, the sensor element 14 can be inserted into holder 21 in a direction perpendicular to lead wires 22 and 23.

Figure 8:
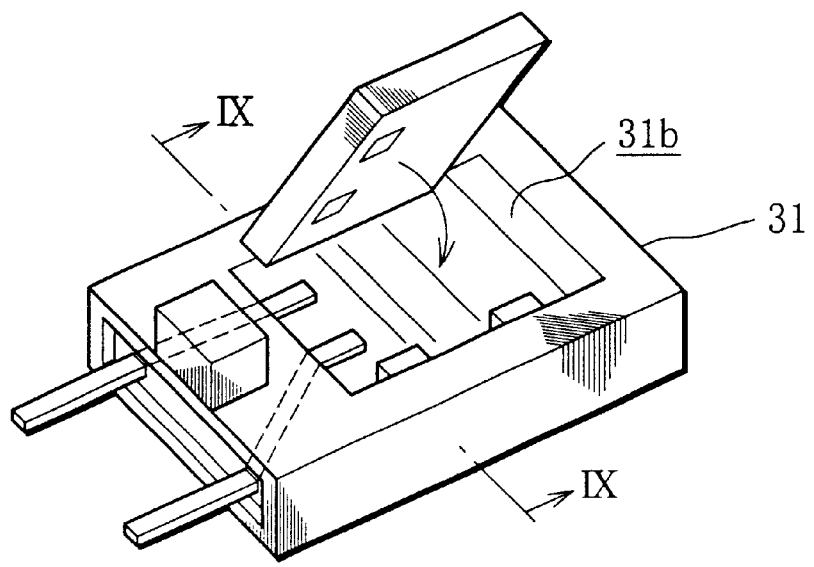
FIG. 8 is a schematic perspective view showing a humidity sensor according to another embodiment of the invention.
Figure 9:
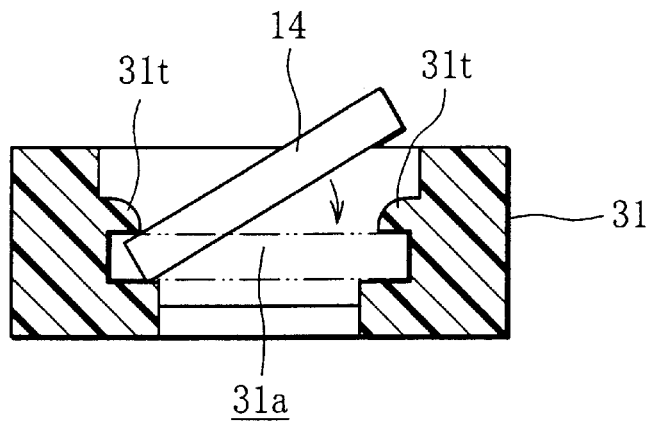
FIG. 9 is a sectional view of the detector taken along line IX—IX of FIG. 8.

Further, a sensor element loading aperture 31b may be formed in the rear face (upper surface in FIG. 8) of a holder 31, as shown in FIG. 8, while latch claws 31t capable of elastic deformation may be formed on the inner wall of a sensor element storage portion 31a, as shown in FIG. 9. Thus, the sensor element 14 can be inserted through the rear face of the holder 31 and held latched in the element storage portion 31a of the holder.

In the embodiment described above, the space (X in FIG. 2) between the lead wires in the storage portion of the holder is expected only to allow the resin conductors to be applied with ease. Therefore, this space need not always be changed with respect to the space (Y in FIG. 2) between the lead wires in the outlet portion of the holder.

Further, the lead wires need not always be molded integrally with the holder in advance. Thus, the lead wires may be inserted individually into a pair of lead wire holes in the holder as the humidity sensor is attached.

Even if the lead wires and the electrodes of the sensor element are directly in contact with one another, moreover, the resin conductors can be easily applied to the junctions between them provided that the holder has a connecting aperture through the junctions are exposed. In consequence, there still remains an effect to improve the assembling properties of the humidity sensor considerably.

In the embodiment described above, the detector according to the present invention is applied to the humidity sensor. It is to be understood, however, that the present invention is not limited to this, and may be also applied to various other detectors such as a temperature sensor, magnetic sensor, etc.

EXAMPLE

Figure 10A:
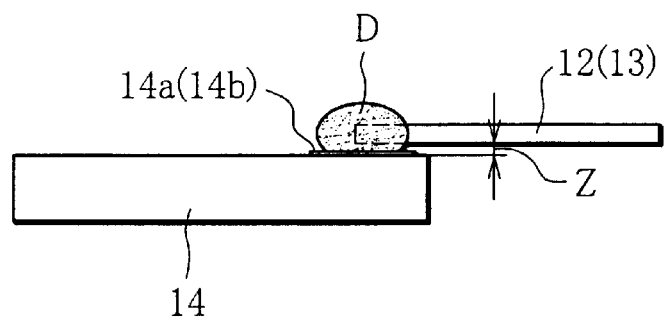
FIG. 10A is a view showing the way a lead wire is bonded to the sensor element of the humidity sensor according to the embodiment of the invention.
Figure 10B:
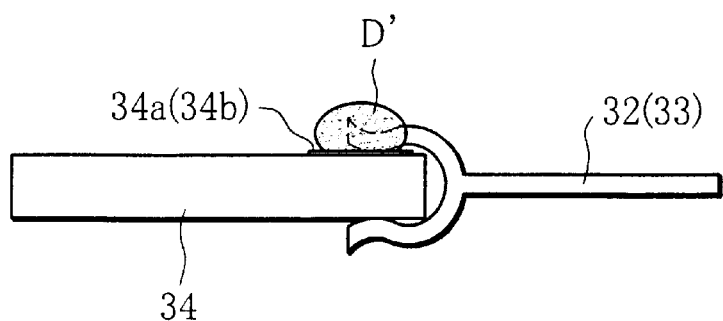
FIG. 10B is a view showing the way a lead wire is bonded to a sensor element of a conventional humidity sensor.

An example of the humidity sensor 10 constructed in this manner (hereinafter referred to as the product of the invention, see FIG. 10A), having the lead wires 12 and 13 and the electrodes 14a and 14b of the sensor element 14 kept at a given distance Z(0.2 mm in this example) and connected electrically to one another by means of the resin conductors D, was checked for detection characteristics. A humidity sensor shown in FIG. 10B was used as a comparative example. In this comparative example, lead wires 32 and 33 are directly in contact with electrodes 34a and 34b, respectively, of a sensor element 34, and their junctions are surrounded by resin conductors D'.

In comparing the product of the invention and the comparative example, a value D was used as an index of evaluation.

The value D is a coefficient that is settled depending on a capacity component $C_s$ and a resistance component $R_s$ of a capacitor, and can be given by $$D = 2\pi f C_s R_s, \qquad (1)$$

where f is frequency (Hz).

If the resistance component $R_s$ changes with time, the value D also changes with time.

Figure 11:
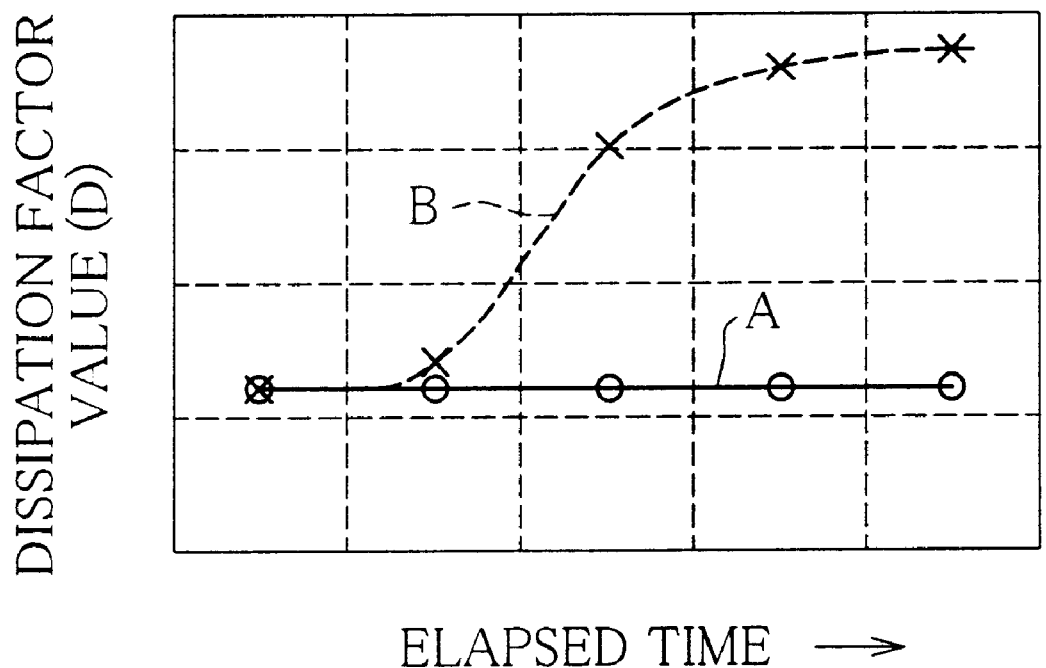
FIG. 11 is a diagram showing the results of an examination for comparison between an example of the invention and a comparative example shown in FIGS. 10A and 10B.

The detection characteristics of the two examples were examined. The examination revealed, as shown in FIG. 11, that the value (D) of the dissipation factor of the product of the invention is constant without regard to the elapsed time (curve A of FIG. 11), while the dissipation factor value (D) of the comparative example increases in proportion to the elapsed time (curve B of FIG. 11). Thus, it was indicated that the dissipation factor value (D) of a conventional humidity sensor past its lifetime is about three times as high as its initial dissipation factor value (D).

In the case of the humidity sensor of the comparative example, the electrodes 34a and 34b of the sensor element 34 and the lead wires are brought directly in contact with one another for electrical conduction. Therefore, the increase of the dissipation factor value of the comparative example is supposed to be attributable to the change of the contact resistance value with time that is caused as contact portions are relatively shifted by vibration or the like after prolonged use of the humidity sensor.

On the other hand, the dissipation factor of the product of the invention is constant for the following reason. The gap Z (0.2 mm) is secured between each electrode 14a (14b) of the sensor element 14 and its corresponding lead wires 12 (13), and the electrodes and the wires are connected electrically to one another by means of the resin conductors. If the electrodes and the wires are dislocated with respect to one another, therefore, the elastic resin conductors can absorb the dislocation, so that the contact resistance value never changes.

As is evident from the results of the examination described above, the humidity sensor according to the foregoing embodiment of the present invention enjoys very reliable detection characteristics that never change with time.

What is claimed is:

1. A detector comprising:
   a detecting element comprising a self-supporting base and electrodes formed on the self-supporting base;
   conducting wires connected individually to the electrodes by means of resin conductors formed of an organic high-molecular resin having an electrically conductive material dispersed therein; and
   a holding member formed of an organic high-molecular resin and accommodating therein the detecting element and the conducting wires,
   wherein the holding member comprises a connecting aperture having a size and location so as to permit junctions between the electrodes and the conducting wires to be fully exposed through the connecting aperture.

2. A detector comprising:
   a detecting element comprising a self-supporting base and electrodes formed on the self-supporting base;
   conducting wires connected individually to the electrodes by means of resin conductors formed of an organic high-molecular resin having an electrically conductive material dispersed therein; and
   a holding member formed of an organic high-molecular resin and accommodating therein the detecting element and the conducting wires,
   wherein the electrodes and the conducting wires are kept apart from one another with spaces therebetween, and the resin conductors are interposed in the spaces to establish electrical connection between the electrodes and the conducting wires.

3. The detector according to claim 1, wherein said holding member comprises a loading aperture through which the detecting element is inserted slidingly.

4. The detector according to claim 2, wherein said holding member comprises a loading aperture through which the detecting element is inserted slidingly.

5. The detector according to claim 1, wherein said holding member comprises an elastically deformable retaining portion for holding the detecting element.

6. The detector according to claim 2, wherein said holding member comprises an elastically deformable retaining portion for holding the detecting element.

7. The detector according to claim 1, wherein said conducting wires are molded integrally with the holding member.

8. The detector according to claim 2, wherein said conducting wires are molded integrally with the holding member.

9. The detector according to claim 1, wherein said holding member comprises a ventilation aperture through which the detecting element is exposed, and said holding member comprises a protecting portion between the ventilation aperture and the connecting aperture.

10. The detector according to claim 1, wherein said holding member comprises a closing member for closing the connecting aperture.

11. The detector according to claim 9, wherein said ventilation aperture and said connecting aperture are covered by a porous filter.

12. The detector according to claim 1, wherein air passages are defined between the detecting element and the holding member, and the air passages are capable of facilitating ventilation between front and rear faces of the detecting element.

13. The detector according to claim 2, wherein air passages are defined between the detecting element and the holding member, and the air passages are capable of facilitating ventilation between front and rear faces of the detecting element.

14. The detector according to claim 1, wherein said detecting element comprises a moisture-responsive surface for humidity detection on a first side face thereof, and each said conducting wire has a first end conducting to an electrode on one side face of the detecting element and a second end led out of the holding member so as to extend substantially flush with a second side face of the detecting element.

15. The detector according to claim 2, wherein said detecting element comprises a moisture-responsive surface for humidity detection on a first side face thereof, and each said conducting wire has a first end conducting to an electrode on one side face of the detecting element and a second end led out of the holding member so as to extend substantially flush with a second side face of the detecting element.

16. The detector according to claim 1, further comprising a projection formed flush with a wire outlet surface of the holding member, wherein said projection is adapted to prevent the holding member from falling down when the holding member is mounted on the base with the wire outlet surface of the holding member in contact with the base.

17. The detector according to claim 2, further comprising a projection formed flush with a wire outlet surface of the holding member, wherein said projection is adapted to prevent the holding member from falling down when the holding member is mounted on the base with the wire outlet surface of the holding member in contact with the base.

18. The detector according to claim 1, wherein said conducting wires include two lead wires attached substantially parallel to the holding member, and a pitch between extending portions of the lead wires extending from the holding member is different from a pitch between resin conductor bonding portions of the lead wires.

19. The detector according to claim 2, wherein said conducting wires include two lead wires attached substantially parallel to the holding member, and a pitch between extending portions of the lead wires extending from the holding member is different from a pitch between resin conductor bonding portions of the lead wires.

* * * * *